(12) United States Patent
Sakai et al.

(10) Patent No.: US 12,132,868 B2
(45) Date of Patent: Oct. 29, 2024

(54) TELEPRESENCE SYSTEM

(71) Applicant: SONY GROUP CORPORATION, Tokyo (JP)

(72) Inventors: Yusuke Sakai, Tokyo (JP); Masahiro Yamaguchi, Aichi (JP); Yosuke Fujimoto, Aichi (JP)

(73) Assignee: SONY GROUP CORPORATION, Tokyo (JP)

( * ) Notice: Subject to any disclaimer, the term of this patent is extended or adjusted under 35 U.S.C. 154(b) by 49 days.

(21) Appl. No.: 17/781,992

(22) PCT Filed: Nov. 27, 2020

(86) PCT No.: PCT/JP2020/044182
§ 371 (c)(1),
(2) Date: Jun. 2, 2022

(87) PCT Pub. No.: WO2021/117503
PCT Pub. Date: Jun. 17, 2021

(65) Prior Publication Data
US 2023/0007127 A1    Jan. 5, 2023

(30) Foreign Application Priority Data

Dec. 13, 2019  (JP) ................. 2019-225443

(51) Int. Cl.
*H04M 3/56* (2006.01)
*A61L 9/00* (2006.01)
(Continued)

(52) U.S. Cl.
CPC .............. *H04M 3/567* (2013.01); *A61L 9/00* (2013.01); *G06F 3/011* (2013.01); *H04N 13/302* (2018.05);
(Continued)

(58) Field of Classification Search
CPC ....... H04M 3/567; A61L 9/00; A61L 2209/11; G06F 3/011; G06F 2203/011;
(Continued)

(56) References Cited

U.S. PATENT DOCUMENTS

| 9,922,463 | B2 * | 3/2018 | Lanier | ................. G02B 27/017 |
| 2008/0079800 | A1 * | 4/2008 | Kobayashi | ............. H04N 7/142 |
| | | | | 348/E7.083 |

(Continued)

FOREIGN PATENT DOCUMENTS

| CN | 101155292 A | 4/2008 |
| CN | 108370431 A | 8/2018 |

(Continued)

OTHER PUBLICATIONS

International Search Report and Written Opinion of PCT Application No. PCT/JP2020/044182, issued on Feb. 9, 2021, 09 pages of ISRWO.

*Primary Examiner* — Yosef K Laekemariam
(74) *Attorney, Agent, or Firm* — CHIP LAW GROUP

(57) ABSTRACT

There is provided a telepresence system that includes a network that connects a plurality of bases, and a plurality of telepresence apparatuses that transmit and receive video images and sound via the network, and share the video images and the audio between the respective bases. Further, in each of the telepresence apparatuses, a presentation device that performs presentation for prompting communication by users at different bases is disposed at the center of a shared communication space in which the users communicate with each other.

9 Claims, 12 Drawing Sheets

(51) Int. Cl.
  *G06F 3/01* (2006.01)
  *H04N 13/302* (2018.01)
  *H04N 13/354* (2018.01)
(52) U.S. Cl.
  CPC ......... *A61L 2209/11* (2013.01); *H04N 13/354* (2018.05)
(58) Field of Classification Search
  CPC ...... H04N 13/302; H04N 13/354; H04N 7/15; H04N 21/431
  See application file for complete search history.

(56) References Cited

U.S. PATENT DOCUMENTS

2018/0332254 A1* 11/2018 Sakai .................... H04N 7/15
2019/0327446 A1   10/2019 Sakai et al.

FOREIGN PATENT DOCUMENTS

| | | |
|---|---|---|
| EP | 3389261 A1 | 10/2018 |
| JP | 2006-191460 A | 7/2006 |
| JP | 2008-085930 A | 4/2008 |
| JP | 2009-239762 A | 10/2009 |
| WO | 2017/098772 A1 | 6/2017 |
| WO | 2017/098780 A1 | 6/2017 |
| WO | WO 2019/096912 * | 5/2019 ............ H04W 68/02 |

* cited by examiner

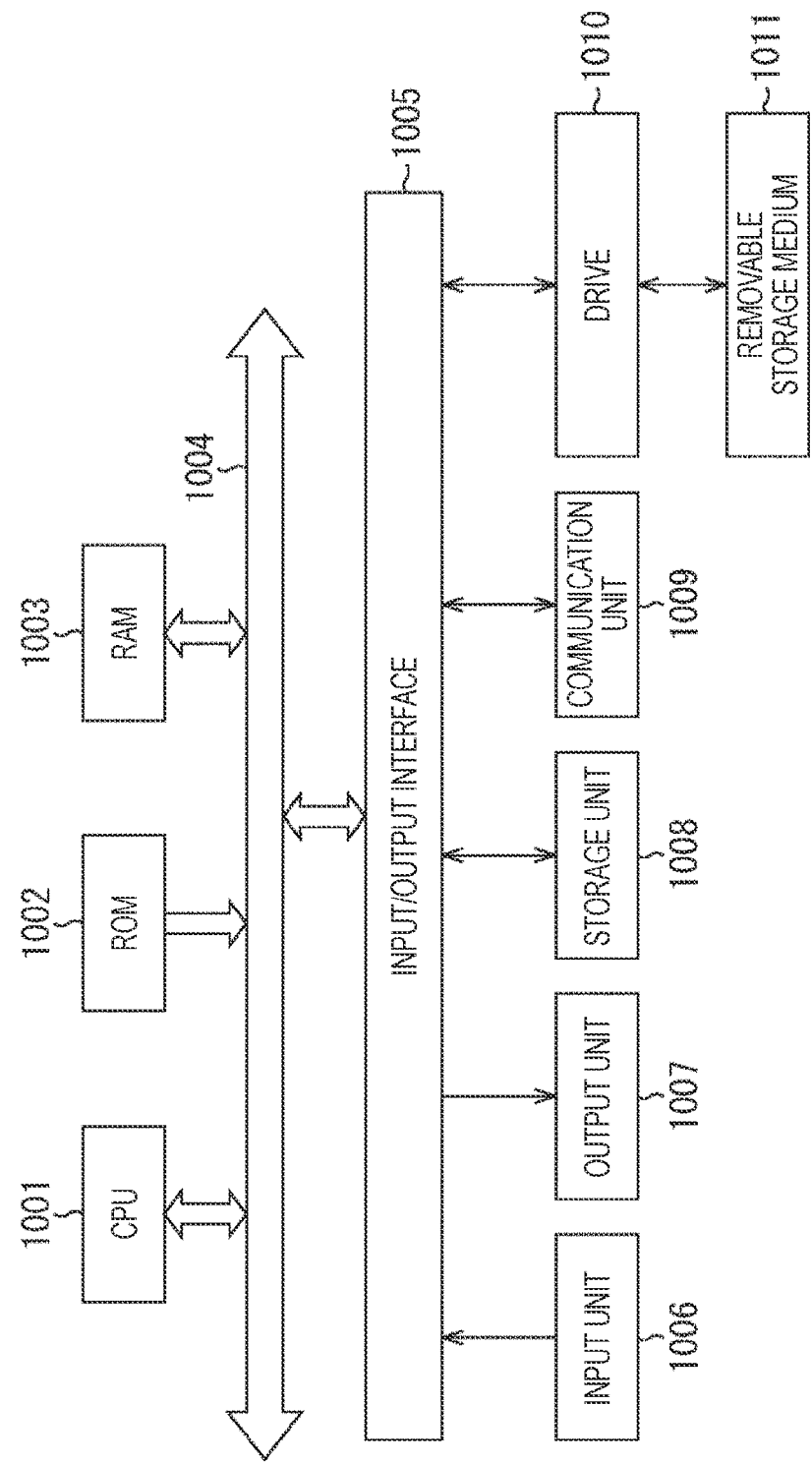

TELEPRESENCE SYSTEM

CROSS REFERENCE TO RELATED APPLICATIONS

This application is a U.S. National Phase of International Patent Application No. PCT/JP2020/044182 filed on Nov. 27, 2020, which claims priority benefit of Japanese Patent Application No. JP 2019-225443 filed in the Japan Patent Office on Dec. 13, 2019. Each of the above-referenced applications is hereby incorporated herein by reference in its entirety.

TECHNICAL FIELD

The present disclosure relates to a telepresence system, and more particularly, to a telepresence system that enables better communication.

BACKGROUND ART

Telepresence systems have been developed to connect distance spaces to each other by video image, sound, and other information channels, and make users feel as if the places were continuous and each other were actually there.

For example, in a case where a parent and a child live apart from each other, a telepresence system enables them to see their living spaces are continuous via a window or a door. Further, in a case where their living spaces are connected to each other by the telepresence system, each user can live while roughly grasping the state of the other space (such as the state of the child or the state of the parent, for example).

For example, as disclosed in Patent Documents 1 and 2, a suggested telepresence system is capable of producing a distance to the other side of communication by using a three-dimensional expression for spatial connection, and achieving more comfortable communication.

CITATION LIST

Patent Document

Patent Document 1: WO 2017/098772 A
Patent Document 2: WO 2017/098780 A

SUMMARY OF THE INVENTION

Problems to be Solved by the Invention

However, telepresence systems such as the one described above have various possibilities, and need to adopt various new ideas for enabling better communication.

The present disclosure is made in view of such circumstances, and aims to enable better communication.

Solutions to Problems

A telepresence system according one aspect of the present disclosure includes: a network that connects a plurality of bases; and a plurality of telepresence apparatuses that transmit and receive a video image and sound via the network, and share the video image and the sound between the respective bases. In each of the telepresence apparatuses, a presentation device that performs presentation for prompting communication by users at different bases is disposed at the center of a shared communication space in which the users communicate with each other.

In one aspect of the present disclosure, a telepresence system includes: a network that connects a plurality of bases; and a plurality of telepresence apparatuses that transmit and receive video images and sound via the network, and share the video images and the audio between the respective bases. Further, each of the telepresence apparatuses includes a presentation device, and the presentation device that performs presentation for prompting communication by users at different bases is disposed at the center of a shared communication space in which the users communicate with each other.

BRIEF DESCRIPTION OF DRAWINGS

FIG. 12 is a block diagram showing an example configuration of an embodiment of a computer to which the present technology is applied.

MODE FOR CARRYING OUT THE INVENTION

The following is a detailed description of specific embodiments to which the present technology is applied, with reference to the drawings.

Example Configuration of a Telepresence System

Figure 1:
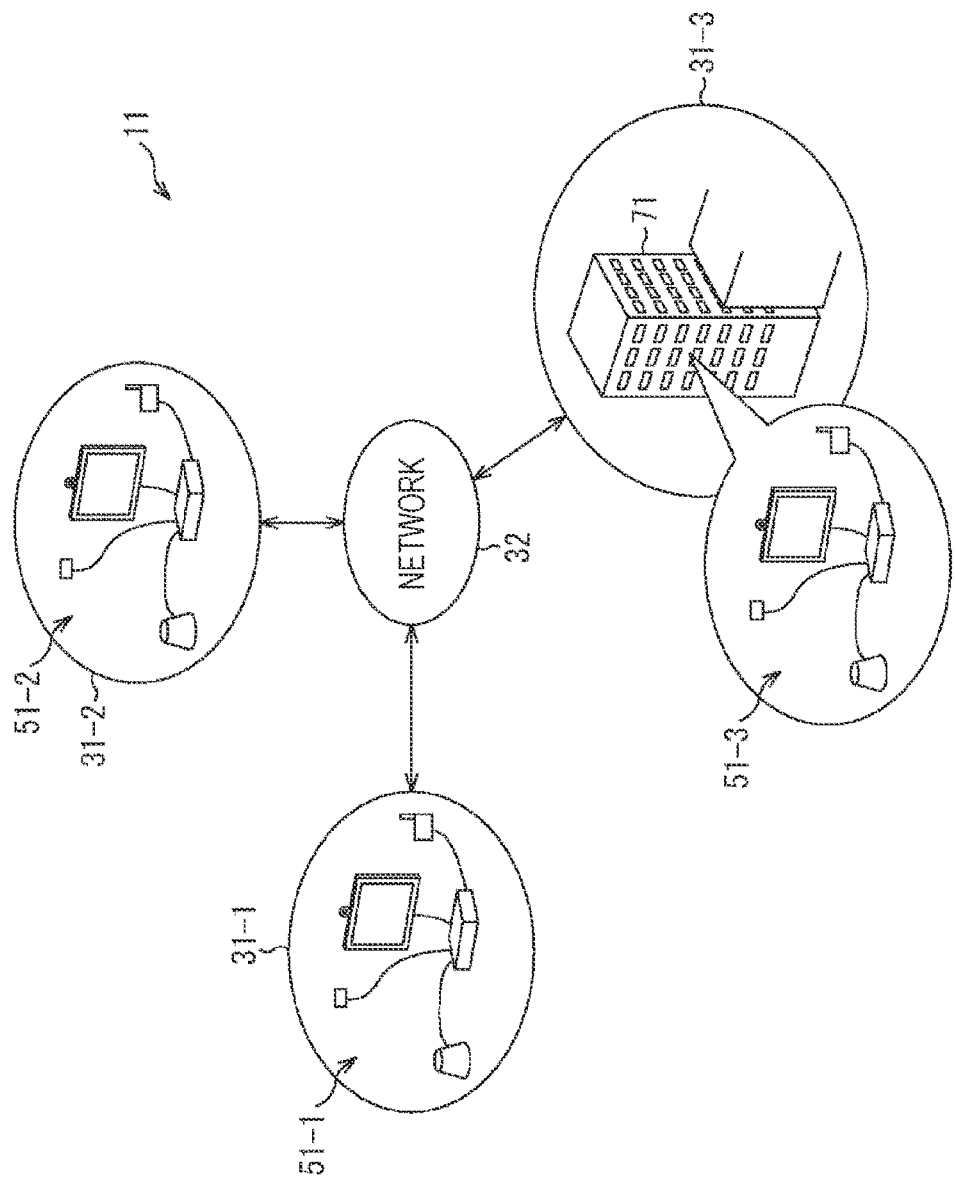
FIG. 1 is a diagram showing an example configuration of an embodiment of a telepresence system to which the present technology is applied.

FIG. 1 is a diagram showing an example configuration of an embodiment of a telepresence system to which the present technology is applied.

The telepresence system 11 shown in FIG. 1 includes three bases 31-1 to 31-3 that are connected via a network 32. Note that the telepresence system 11 may have a configuration in which two bases 31 are connected, or three or more bases 31 are connected.

For example, the bases 31-1 and 31-2 are outdoor environments such as camping sites, and telepresence apparatuses 51-1 and 51-2 are provided in the respective bases. Meanwhile, the base 31-3 is an indoor environment such as an office building 71, and a telepresence apparatus 51-3 is provided therein. Note that, in a case where there is no need to distinguish the bases 31-1 to 31-3 from one another and the telepresence apparatuses 51-1 to 51-3 from one another, they are simply referred to as bases 31 and telepresence apparatuses 51, and other components are also referred to in a similar manner. Also, a plurality of telepresence apparatuses 51 may be provided in one base 31.

Further, in the telepresence system 11, telepresence apparatuses 51 designed in similar manners are provided in a plurality of bases 31, and video images and sound are transmitted and received via the network 32. With this arrangement, the video images and the sound are shared among the respective bases 31, and the users who are using the respective telepresence apparatuses 51 can experience telepresence. For example, telepresence is realized so that users at different bases 31 can interact with each other as if they were in the same place.

Also, in the telepresence system 11, the telepresence apparatus 51-3 at the base 31-3 set in the office building 71 shares the outdoor environment (including a video image and the like) of the base 31-1 or 31-2 with the telepresence apparatus 51-1 or 51-2. Accordingly, the user using the telepresence apparatus 51-3 can experience telepresence as if the user were in an outdoor environment like the base 31-1 or 31-2, for example. Also, the telepresence system 11 may be designed so that that video images and sound can be shared between indoor bases 31 or between outdoor bases 31.

As described above, a user who is using the telepresence system 11 can experience telepresence as if the user were sharing space and having communication with a user at a spatially distant base 31 via the network 32. In the telepresence realized by the telepresence system 11 described below, the virtual space in which communication is performed as if shared by users, which is the entire space over the network 32, will be referred to as the communication space, as appropriate.

Figure 2:
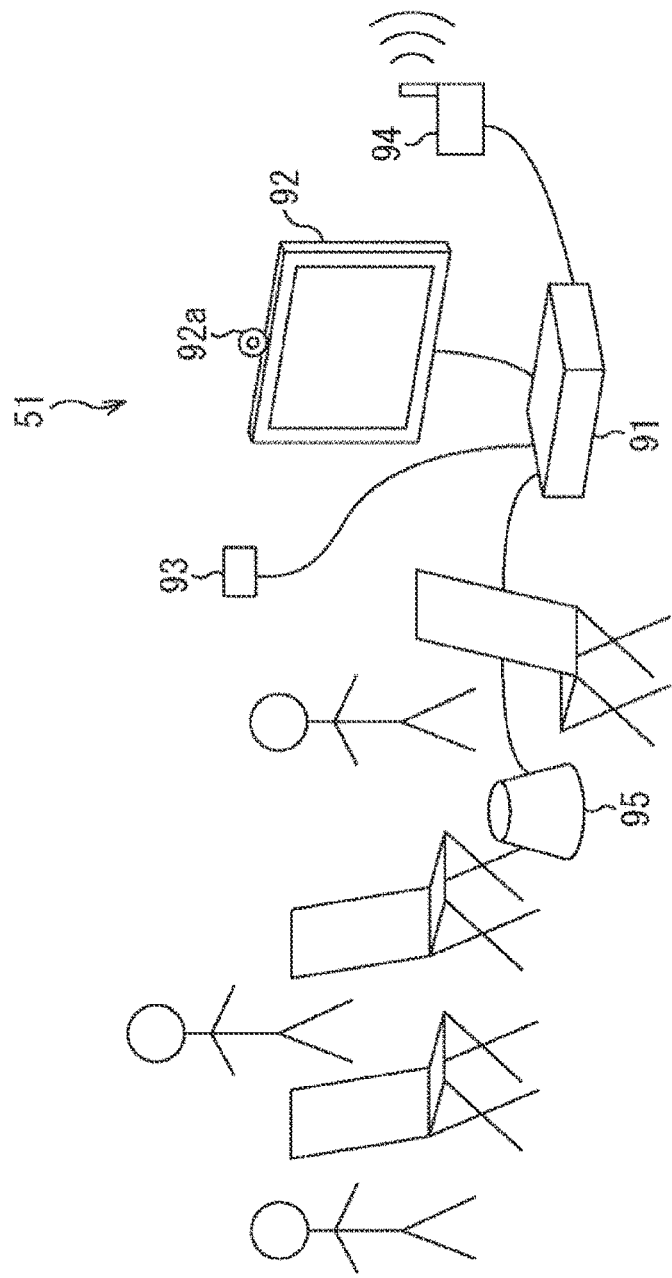
FIG. 2 is a diagram showing an example configuration of a telepresence apparatus.

Referring now to FIG. 2, an example configuration of a telepresence apparatus 51 is described.

As shown in FIG. 2, a telepresence apparatus 51 includes an information processing device 91, a display device 92, a sensing unit 93, an antenna 94, and a central presentation device 95.

The information processing device 91 includes a personal computer or the like, for example, and controls the respective components constituting the telepresence apparatus 51, to realize telepresence in the telepresence system 11.

The display device 92 includes a light emitting diode (LCD), an organic electro-luminescence (EL), a projector, or the like, for example, and displays a video image supplied via the information processing device 91. For example, the display device 92 displays a video image that has been captured by a user who is using another telepresence apparatus 51 and been transmitted from another base 31. Further, the display device 92 includes an imaging unit 92a that images users who are using the telepresence apparatus 51, and transmits a video image obtained through the imaging to another base 31 via the information processing device 91. Note that the display device 92 includes a speaker (not shown), and can output a voice transmitted from another base 31 so as to be heard from the position of the user who has uttered the voice.

The sensing unit 93 senses an emotion, biological information, various states, and the like of the users experiencing telepresence using the telepresence system 11. The sensing unit 93 also senses the context of communication between a plurality of users using the telepresence system 11, various situations, and the like. The sensing unit 93 then supplies sensing information indicating the results of the sensing to the information processing device 91.

The antenna 94 is connected to a communication unit 112 (shown in FIG. 9, which will be described later) of the information processing device 91, and transmits and receives radio waves for performing wireless communication via the network 32, for example.

The central presentation device 95 is disposed at the position to be the center of the communication space in the telepresence to be realized by the telepresence system 11. For example, the central presentation device 95 is not disposed at the actual center of a plurality of users present at one base 31, but is disposed at a virtual center of users including a plurality of users present at another base 31 displayed on the display device 92.

For example, when a plurality of users has an interaction, the users face each other during the interaction. As the number of users increases, the seats normally form a ring so that the users sit in a circle. Likewise, when a plurality of users present at different bases 31 has an interaction using the telepresence system 11, the users are likely to be sit in a ring. In other words, even if the users do not exist in the same space, the users are likely to feel as if they were sitting in a ring during an interaction, and recognize such a space and the existence of the users. Further, in the telepresence system 11, the center of the ring formed with the plurality of users at the different bases 31 appears in the vicinity of the display device 92 serving as the boundary virtually connecting the respective spaces, and the central presentation device 95 is preferably disposed in the vicinity (front) of the display device 92.

The central presentation device 95 then performs various kinds of presentation so as to prompt all the users using the telepresence system 11 to share the communication space and have preferable communication. For example, the central presentation device 95 can present a virtual bonfire by outputting a video image, sound, light, heat, a scent, and the like of a bonfire, for example.

Figure 3:
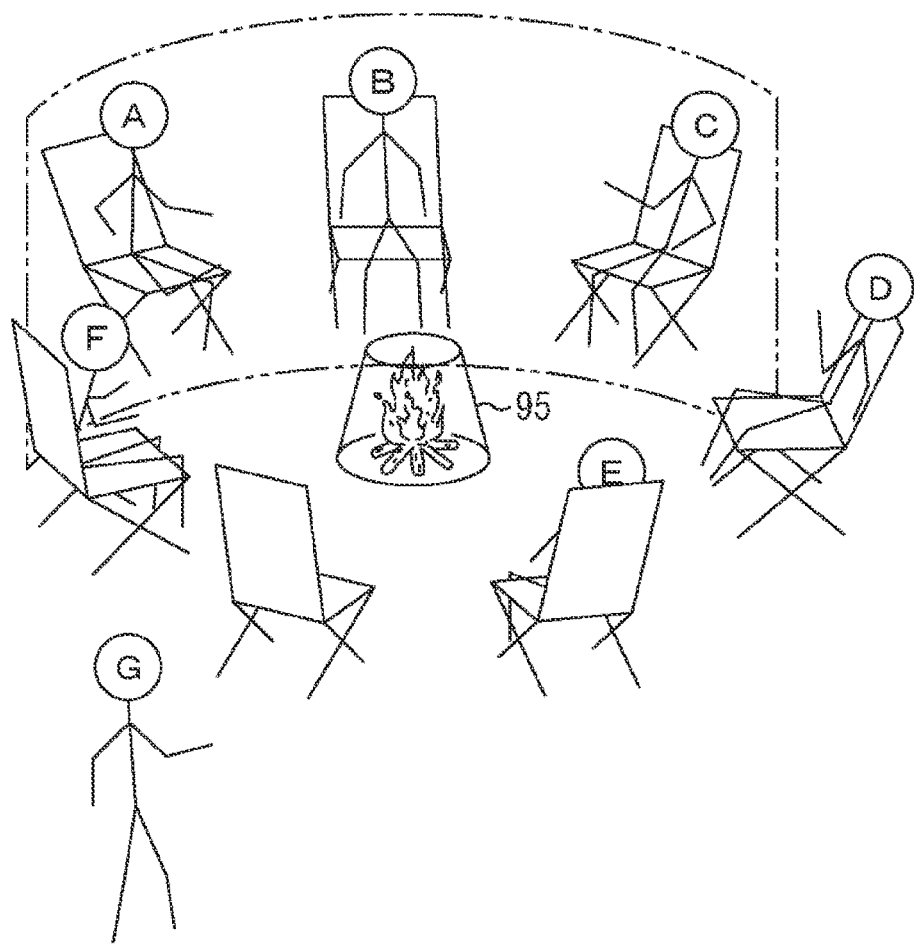
FIG. 3 is a diagram for explaining a first situation in a communication space.

Referring now to FIG. 3, a first situation in a communication space realized by the telepresence system 11 is described.

As shown in FIG. 3, users A to G present at two bases 31, with a bonfire being presented by the central presentation device 95 at the center, for example, can experience telepresence that shares a communication space as if surrounding one bonfire over the distance.

Here, the base 31 at which the users A to C surrounded by a double-dot-and-dash line in FIG. 3 among the users A to G are present is also referred to as the other base 31, and the base 31 at which the other users D to G are present is also referred to as the subject base 31. For example, the users A to C at the other base 31 are displayed in a life size on the display device 92 of the subject base 31. At this point of time, the display device 92 can create a communication space in which the users A to G at the two bases 31 surround the central presentation device 95 at the center, using an arc-shaped display (such as a projector that projects a video image onto an arc-shaped screen, for example) shown by the double-dot-and-dash line. Further, the display device 92 is preferably formed with a transparent or semi-transparent display, so that the users A to C at the other base 31 are displayed as if floating in the air, and the landscape of the subject base 31 is visible behind the users A to C.

Meanwhile, the central presentation device 95 stereoscopically outputs a video image of a bonfire, and the users D to G at the subject base 31 can see the bonfire from anywhere around the central presentation device 95. Further, the central presentation device 95 can output sound, heat, light, scent, and the like as experienced with an actual bonfire. With this arrangement, it is possible to emphasize that the same communication space is shared between the users A to C and the users D to G present at the different bases 31, and increase the realistic feeling.

Furthermore, like the user G shown in FIG. 3, it is possible to freely view the communication space from a distance away from the positions surrounding the central presentation device 95 and return into the communication space.

Note that the central presentation device 95 is disposed so as not to be imaged by the imaging unit 92a, and is not displayed on the display device 92 at the base 31 on the other side. With this arrangement, the users at each base 31 can feel as if one bonfire presented by the central presentation device 95 of each base 31 were placed at the center of the communication space.

As described above, the bases 31 at distant places are connected, and the users at the respective bases 31 are connected, with the bonfire presented by the central presentation device 95 being placed at the center. In this manner, communication can be made more active. In other words, the users who are using the telepresence system 11 can go through an experience to enhance the creativity as a more united team with a feeling as if surrounding the same bonfire, and can achieve multi-modal bidirectional communication.

That is, using the telepresence system 11, it is possible to achieve an effect to make the conversation more active, as the plurality of users sits in a circle surrounding the bonfire. Also, even in a situation where two users face each other on a one-to-one basis, such a bonfire makes it easier to draw out the individuality of each other, and psychological safety can be enhanced as the conversation progresses. Further, feeling the heat, the light, and the scent of the bonfire, the users can relax more, and have communication with flexible mindset.

Also, using the telepresence system 11, it is possible to immediately have close communication even with colleagues working at a distant place, for example, without having to worry about superior-inferior relationship or the like. In such a case, with a conventional general-purpose conference system, for example, it is likely that the users are too nervous to have smooth communication. With the telepresence system 11, however, more relaxed communication can be performed.

Note that the telepresence system 11 can have functions such as a face authentication sign-in function using an image of a user captured by the imaging unit 92a, a device control function using speech recognition, and a device cooperation function using a terminal like a smartphone.

Also, in the telepresence system 11, the bases 31-1 and 31-2 such as camping sites, and the base 31-3 such as the office building 71 can be always connected via the network 32. In the telepresence system 11, the degree of connection, the display balance, and the like between the bases 31 are then adjusted so that the users at the other bases 31 are displayed in life size at each base 31. Further, in the telepresence system 11, the position of the imaging unit 92a of each base 31 is designed so that that the lines of sight of the users meet in the communication space.

Figure 4A:
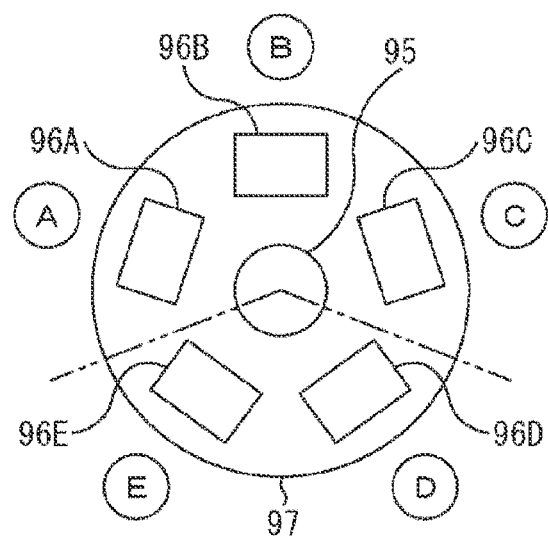
FIGS. 4A and 4B are diagrams for explaining a second situation in a communication space.
Figure 4B:
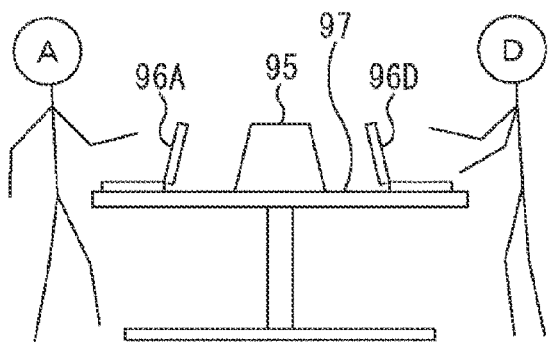

Referring now to FIGS. 4A and 4B, a second situation in a communication space realized by the telepresence system 11 is described.

As shown in FIGS. 4A and 4B, for example, users A to E present at two bases 31 can experience telepresence sharing a communication space as if surrounding a round table 97 on which the central presentation device 95 is placed. For example, the central presentation device 95 may include a mechanism that rotates at the center of the round table 97, a mechanism that rises from the inside of the round table 97, or the like. In the telepresence system 11, personal computers 96A to E are also placed on the round table 97 for the respective users A to E.

Here, the base 31 at which the users A to C on one side of a double-dot-and-dash line in FIGS. 4A and 4B among the users A to E are present is also referred to as the other base 31, and the base 31 at which the users D and E on the other side are present is also referred to as the subject base 31.

In this manner, the telepresence system 11 can be used to achieve communication between the users A to C and the users D and E at the different bases 31, in a communication space having a layout (hereinafter referred to as a round-table layout.) in which the users A to E are seated so as to surround the central presentation device 95 provided at the center of the round table 97.

For example, when telepresence in the round-table layout is used in the telepresence system 11, conversations, ideas, and the like become smoother, and conferences, meetings, and the like can be held in a preferred manner. Further, a conference in the round-table layout prompts the users to more actively participate in the conference.

Also, in the telepresence system 11, information shared by all the users is displayed on the central presentation device 95, so that the central presentation device 95 can be used as a means for sharing information like a whiteboard that is used in a general conference, for example. With this arrangement, the telepresence system 11 can be used in such a manner that all the users participating in a conference face one another at the same time, for example, and visually recognize and share the information displayed on the central presentation device 95.

For example, the telepresence system 11 can be used in such a manner that the information to be viewed individually by the respective users is displayed on the personal computers 96, and the information to be shared by all the users is displayed on the central presentation device 95. For example, by making the central presentation device 95 rotatable, it becomes possible for each user to easily write or view information. Note that, in the telepresence system 11, in a case where any information is not shared through the central presentation device 95, a video image of a bonfire may be displayed as described above, or some other purposeless video image may be displayed, so that a plurality of users can perform work while sharing such video images.

Here, the round table 97 is a space shared for interaction by a plurality of users, and is a work space, for example. Also, the round table 97 is a space in which the users at the respective bases 31 can work, and the round table 97 at the other base 31 is displayed on the display device 92 at the subject base 31 as if continuous between the subject base 31 and the other base 31. Further, by presenting the same vibration in the round table 97 at each base 31, it is possible to emphasize that the users at the different bases 31 share the same communication space, and the realistic feeling can be enhanced.

Also, the central presentation device 95 at each base 31 presents common content, and performs physically multi-view or time-division fair presentation so that the content can be shared by all the users at the respective bases 31. Further, the central presentation device 95 can use a stereoscopic display that can be viewed from a plurality of angles, a projector that stereoscopically projects a video image, or the like.

Also, in the telepresence system 11, the central presentation device 95 in a communication space is preferably placed at equal distances from a plurality of users.

Figure 5A:
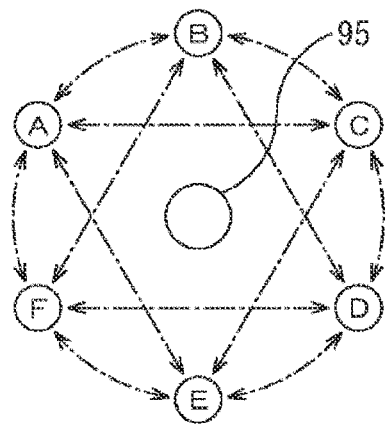
FIGS. 5A, 5B, and 5C are diagrams for explaining setting of a sense of distance between users in a communication space.
Figure 5B:
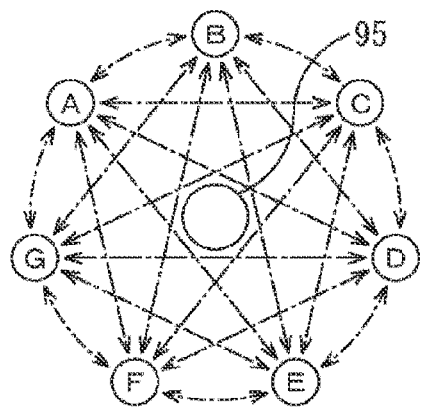
Figure 5C:
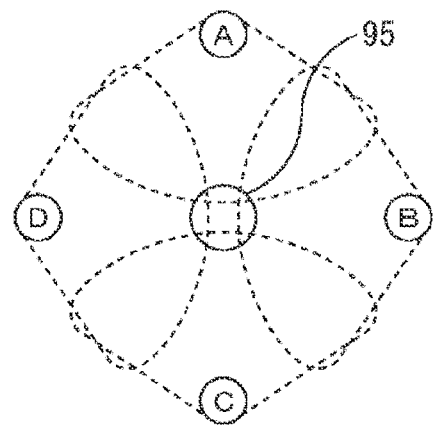

Referring now to FIGS. 5A, 5B, and 5C, distance sense setting in a communication space realized by the telepresence system 11 is described.

For example, in a case where six users A to F use the telepresence system 11 as shown in FIG. 5A, the users are preferably seated at the positions equivalent to the vertices of a regular hexagon so that the distances between the adjacent users in the positional relationship in the communication space are substantially equal. Also, the users are preferably seated so that the distances between the users on the diagonal lines are substantially equal.

The central presentation device 95 is then placed at the center of gravity of a figure formed with the external straight lines connecting the users A to F surrounding the central presentation device 95 in the communication space, and is preferably equidistant from the respective users A to F. With such a sense of distance, the users A to F can have better communication.

Like of FIG. 5A, FIG. 5B shows the layout of the users in a case where seven users A to G use the telepresence system 11, in which the users are preferably seated at the positions corresponding to the vertices of a regular heptagon. The central presentation device 95 is then placed so as to be equidistant from the respective users A to G.

Further, in FIG. 5C, the personal spaces (the ranges that can be reached by hand, for example) of users A to D are indicated by dashed lines. As shown in FIG. 5C, in the telepresence system 11, the central presentation device 95 is placed on the boundaries between the personal spaces of the respective users A to D, and the sense of distance is such that the personal spaces of the users adjacent to each other in the communication space overlap each other. With such a sense of distance, the users A to D can have better communication.

Here, in the telepresence system 11, the distance between the users is preferably set between a distant phase in terms of individual distances in proxemics (for example, a distance at which the person on the other end can be reached by hand: 0.75 to 1.2 m), and an adjacent phase in terms of social distances in proxemics (for example, a distance at which a person can easily have a conversation with the person on the opposite side but cannot reach the person on the opposite side by hand: 1.2 to 2 m). Specifically, in the telepresence system 11, the distance between users is preferably set so as to be felt like about 1 to 2 m, or at a distance longer than that. Accordingly, the telepresence system 11 is most suitable for communication in which about six to eight persons surround the central presentation device 95.

Further, as described below with reference to FIGS. 6A and 6B, the ratio between the regions occupied by a plurality of bases 31 in a communication space can be changed in the telepresence system 11.

Figure 6A:
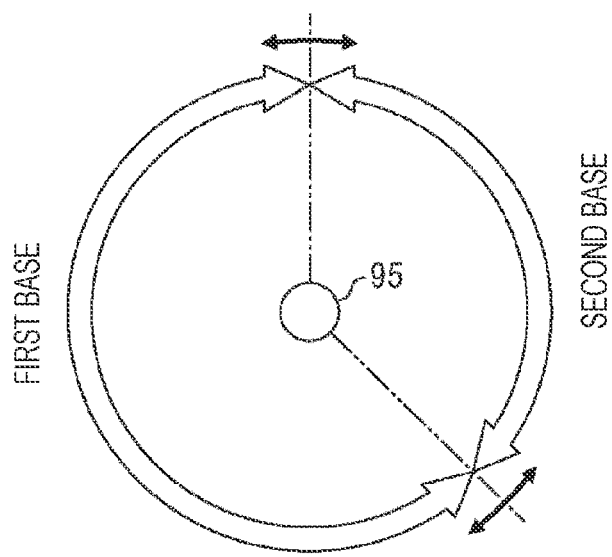
FIGS. 6A and 6B are diagrams for explaining a change in the ratio between regions occupied by a plurality of bases in a communication space.

For example, in a case where a communication space is formed with a first base 31 and a second base 31 as shown in FIG. 6A, the region occupied by the first base 31 and the region occupied by the second base 31 can be set as indicated by white arrows. Further, in the telepresence system 11, the separators (double-dot-and-dash lines) between the region occupied by the first base 31 and the region occupied by the second base 31 can be moved to change the ratio between the regions occupied by the first base 31 and the second base 31 in the communication space.

Figure 6B:
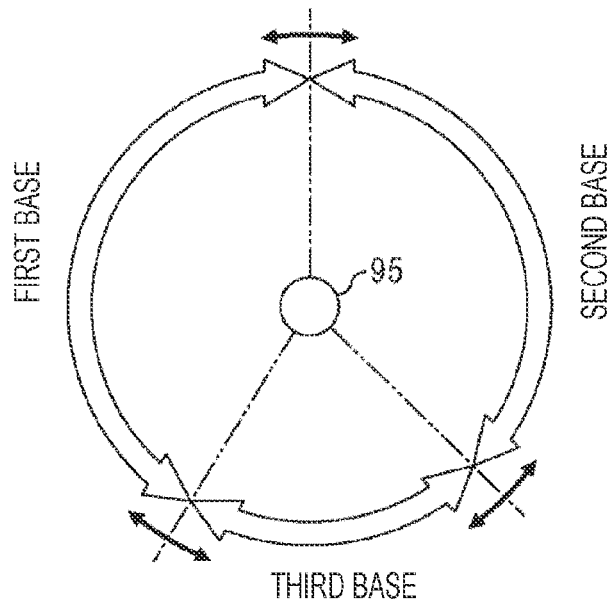

Likewise, as shown in B of FIG. 6B, the ratio among the regions occupied by a first base 31, a second base 31, and a third base 31 in a communication space can be changed.

For example, the telepresence system 11 can change the ratio between the regions occupied by the respective bases 31 in a communication space, in accordance with the number of users present at the plurality of bases 31. That is, when the number of users at a certain base 31 has increased, the telepresence system 11 can make a change so that the ratio of the region occupied by the certain base 31 becomes higher in the communication space.

Further, as described below with reference to FIG. 7, when displaying video images of a plurality of other bases 31 on the display device 92, the telepresence system 11 can dynamically change the regions in which the video images are to be displayed.

Figure 7:
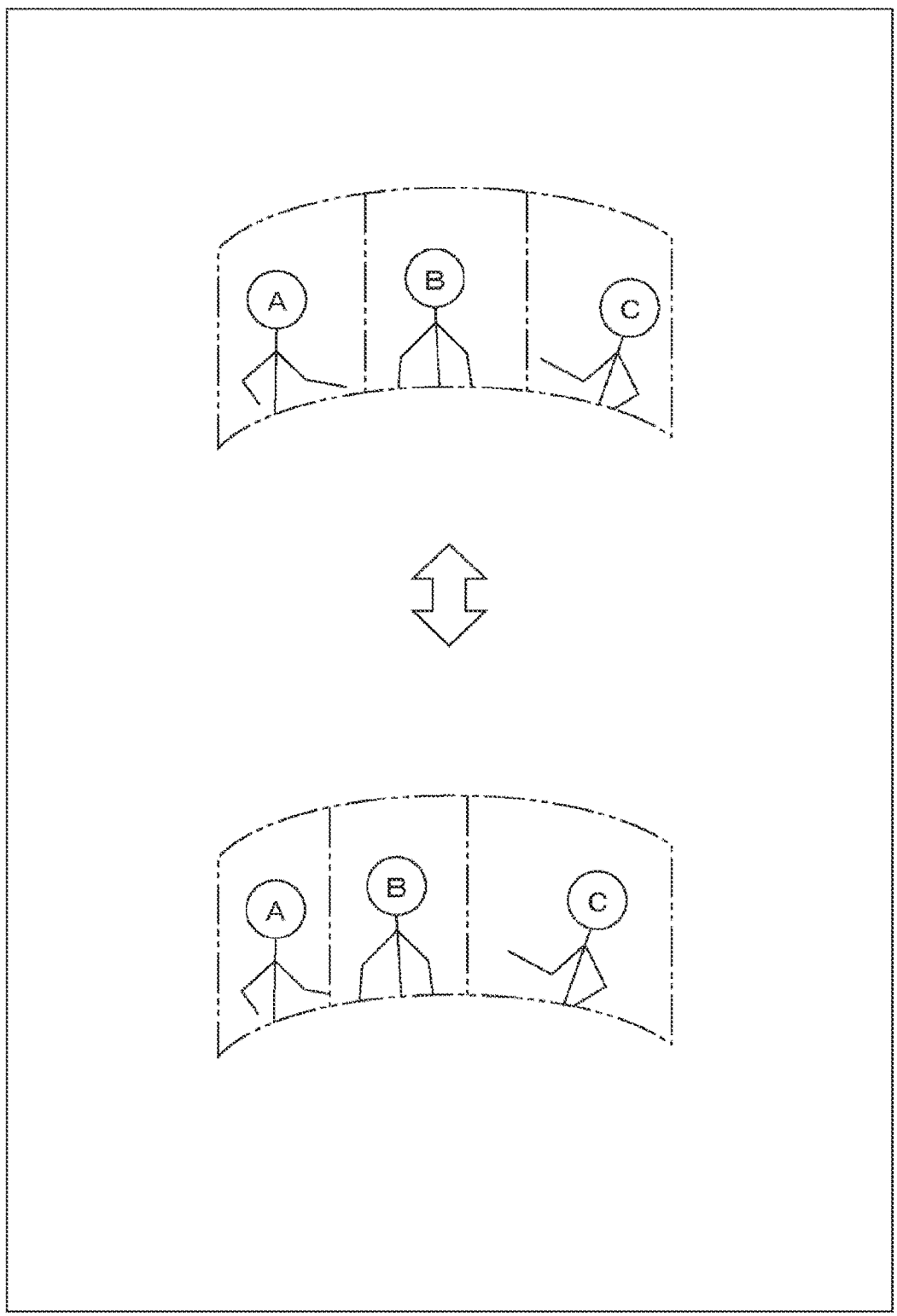
FIG. 7 is a diagram for explaining a change in the ratio between regions displaying video images of a plurality of other bases.

FIG. 7 shows a state in which video images of users A to C present at three other bases 31 are displayed on the display device 92 of the subject base 31. Note that, although not shown in the drawing, users are also present at the subject base 31, as shown in FIG. 3.

For example, as shown on the upper side in FIG. 7, in the initial state of the telepresence system 11, the video images of the users A to C at the respective other bases 31 are equally displayed. The telepresence system 11 then dynamically changes the ratio among the regions displaying the respective video images so that the video image of the user who is talking at the other base 31 more than the others is displayed in a larger size, for example.

For example, in a case where the user C is talking, the ratio of each region is automatically changed so that the region displaying the video image of the user C becomes larger than the regions displaying the video images of the users A and B, as shown on the lower side in FIG. 7. After that, when the user C finishes talking, the video images of the users A to C are automatically returned to equal displays, as shown on the upper side in FIG. 7.

In the user interface that displays video images in this manner, when the ratio among the regions displaying the video images of the users at the respective other bases 31 is changed, the round tables 97 (FIGS. 4A and 4B) at the other bases 31 are displayed on the display device 92 in a fixed manner. Alternatively, when the ratio among the regions displaying the video images of the users at the respective other bases 31 is changed, the round tables 97 at the other bases 31 may also be changed on the display device 92.

Further, in a case where there is the need to crop the video images in accordance with a change in the ratio among the regions displaying the video images of users present at the respective other bases 31, each cropped video image is displayed in a vertically long form. In this case, the video images are neither enlarged nor reduced so that the life size (full scale) is maintained in the displays. Further, the video images may be moved in a lateral direction along the circumference. Alternatively, the layout of the video images of the users at the respective other bases 31 may be dynamically changed. Further, only the regions showing the users may be cut out, and be combined with a common background.

Furthermore, as described below with reference to FIG. 8, in the telepresence system 11, layouts can be switched.

Figure 8:
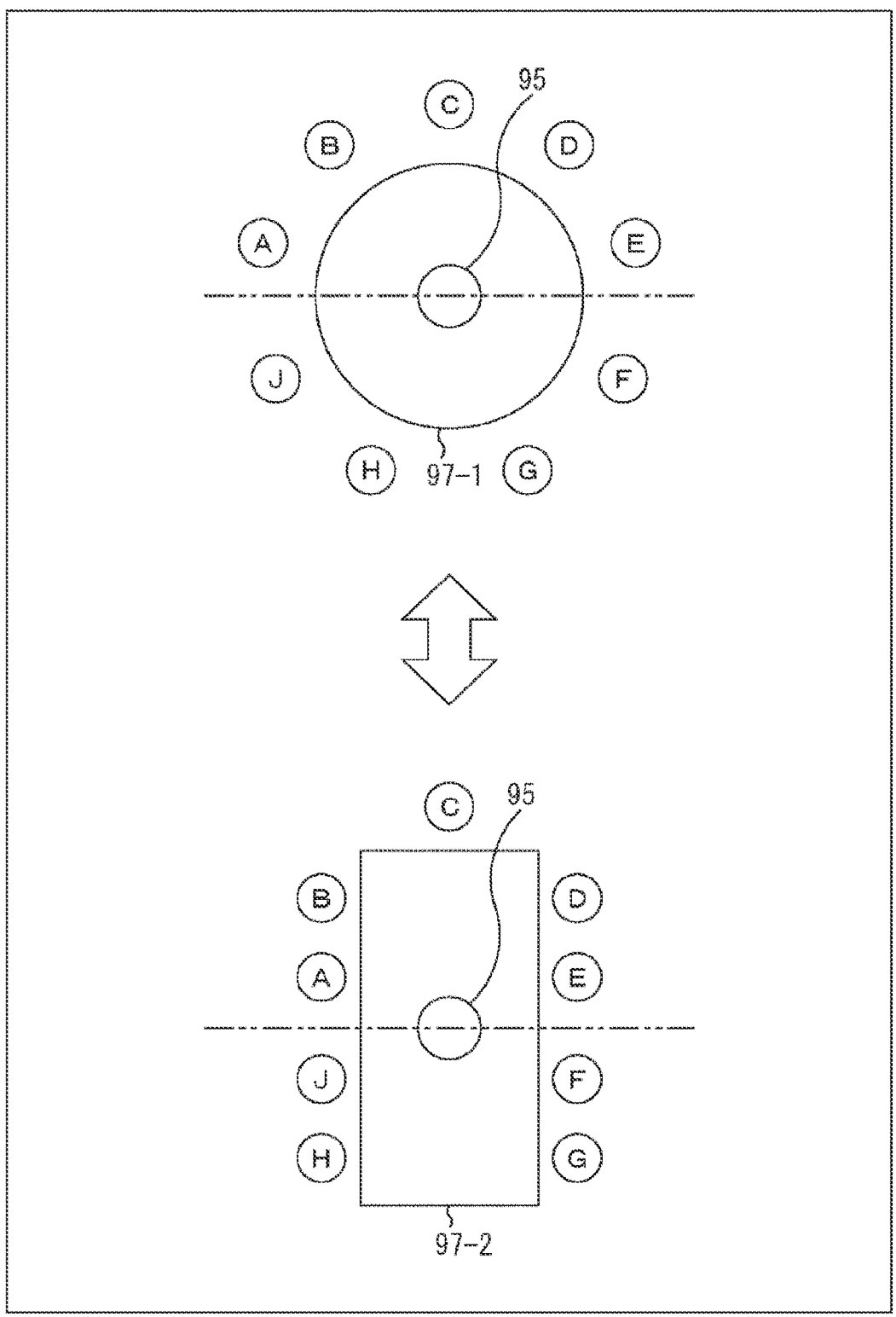
FIG. 8 is a diagram for explaining layout switching.

The upper side in FIG. 8 shows a top view of the round-table layout that is designed so that users surround a round table 97-1 as shown in FIGS. 4A and 4B. Also, the lower side in FIG. 8 shows a top view of a layout (hereinafter referred to as an alignment layout) in which users are seated at one end and along both sides of a long table 97-2 that is normally used in a conference.

As shown in FIG. 8, users A to J at two bases 31 can experience telepresence that shares a communication space so as to surround the round table 97-1 or to line up along the long table 97-2. Although not shown in FIG. 8, personal computers 96A to 96J are also provided for the respective users A to J, as in the case illustrated in FIGS. 4A and 4B.

Here, the base 31 at which the users A to E on one side of a double-dot-and-dash line in FIG. 8 among the users A to J are present is also referred to as the other base 31, and the base 31 at which the users F to J on the other side are present is also referred to as the subject base 31.

In a case where the telepresence system 11 determines that it is necessary to perform relaxed communication on the basis of sensing information, the round-table layout is then selected. For example, in the case of the round-table layout, the users A to E at the other base 31 and the users F to J at the subject base 31 are seated along the round table 97-1 so as to surround the central presentation device 95 at the center. For example, the round-table layout is suitable for sharing vision, and is more useful when used by a team having no upper limit relationship or by six or more users.

In a case where the telepresence system 11 determines that it is necessary to perform intensive communication, on the other hand, the alignment layout is selected. For example, in the case of the alignment layout, the users A and B at the other base 31 and the users H and J at the subject base 31 are seated along one side of the long table 97-2 so as to face the users D and E at the other base 31 and the users F and G at the subject base 31 seated along the other side, and the user C is seated at one end of the long table 97-2. The alignment layout is suitable for achieving greater efficiency, for example.

For example, switching between the round-table layout and the alignment layout can be performed by hardware changing the layout of the round table 97-1 and the long table 97-2 prepared at each base 31. Alternatively, the switching can be virtually performed by changing the display (or the expression of the user interface) of the round table 97-1 and the long table 97-2 in the video image of the other base 31 displayed on the display device 92. Also, when the positions of the respective users are changed from a surrounding form to an alignment form, the layout may be randomly changed.

Further, the telepresence system 11 can switch between the round-table layout and the alignment layout, on the basis of sensing information (such as users' emotions, biological information, various states, and the like, or communication contexts, various situations, and the like) obtained through sensing performed by the sensing unit 93.

For example, the telepresence system 11 can recognize a context, to determine whether to perform switching in accordance with a user's action, utterance, nod, body movement, or the like, or to determine whether to perform switching on the basis of synchronization of biological information (respiration, heartbeat, brain waves, rhythm) between users, a degree of smile, or the like. For example, when the degree of smile of users who are engaged in a conversation while being relaxed becomes higher, it is determined that an atmosphere for communication is formed, and the round-table layout is started. On the other hand, when the degree of smile of users drops during a conference or a meeting in the alignment layout, it is determined that the communication needs to be made smoother, and the layout is switched to the round-table layout.

Meanwhile, the sensing unit 93 may set all the users in a communication space as sensing targets, or may also set a facilitator of a discussion as a sensing target, for example. Further, in a case where the state of a certain number of the users or the state of a specific user exceeds a preset threshold, it is determined that the communication is active or in a creative state, and the layout can be switched.

Note that layouts may be switched on the basis of a preset scenario (such as a conference program).

As described above, as the telepresence system 11 has the function of switching between the round-table layout and the alignment layout, all the users at a conference, a meeting, or the like can actively participate in discussions with enjoyment, and new ideas can be created. It is also possible to strengthen recognition that the users at the respective bases 31 participate in a conference, a meeting, or the like in the same communication space.

Further, in the telepresence system 11, when layouts are switched, the heights of the lines of sight of the users at each base 31 are changed, for example, so that an environment visually different from usual is obtained, and the users can have a diversion. For example, the positions of the chairs used in the telepresence system 11 are regular positions in the alignment layout, and are switched to lower positions in the round-table layout. The lines of sight can be changed in this manner. In this case, the viewpoint from which the imaging unit 92a performs imaging may be lowered at the side of the other base 31. As the layout switching is combined with a change in the line of sight in this manner, it is possible to more efficiently connect the users present at different bases 31.

Note that, in the telepresence system 11, face authentication, smile determination, or the like is performed, for example, so that users in close communication with each other can be recognized. Also, speech recognition is used, so that words or sentences used in conferences, meetings, and the like can be mined (the frequency or the number of times each word appears is analyzed, for example). Further, the telepresence system 11 can have a function of analyzing bases 31 between which conversations are frequently held, bases 31 between which few conversations are held, and the like.

Also, as the round-table layout and the alignment layout are switched by the telepresence system 11, more space can be saved than in a case where conference rooms and the like for the respective layouts are prepared, for example. Further, in the telepresence system 11, layouts can be easily switched with the use of camping equipment, for example, and a new conceptual space can be created.

Here, the telepresence system 11 is suitable in a situation where the user C performs presentation for unilaterally presenting information to the entire communication space in the alignment layout shown on the lower side in FIG. 8, for example.

Meanwhile, the round-table layout shown on the upper side in FIG. 8 is suitable in a situation where all the users A to J in a communication space have discussions or conversations with one another to achieve co-creation. In this case, the facilitator (or simply the utterer) changes from one user to another, for example. However, a user interface with which the central presentation device 95 performs presentation so as to clearly indicate which user is the facilitator may be used.

Furthermore, the telepresence system 11 can use a layout designed to be used in a situation where users simply relax or enjoy casual conversations, even without the aim to establish communication.

Note that the method for switching these layouts may be a method by which a user interface for issuing a layout switching instruction is presented, and a user changes the layout of the round table 97-1 and the long table 97-2, for example. In addition to that, a mechanism for automatically changing the round table 97-1 and the long table 97-2 may be introduced. For example, in addition to changing the shape of a table that mechanically deforms with the power of a drive unit, the telepresence system 11 may give optimum auxiliary information to the facilitator so as to deform the table into a specific desired shape, and a user may change the shape of the table in accordance with an instruction from the facilitator. Likewise, to change the heights of the lines of sight of users, chairs whose heights are changed by the power of a drive unit may be used, for example. In addition to that, users may change the heights of the chairs in accordance with an instruction from the facilitator.

Further, with the use of a table formed by combining a plurality of parts of the same design with dimensions standardized in advance, for example, it is possible to easily change the form of a round table or a long table by combining the parts, and to switch layouts of these tables. Other possible layouts include a layout in which a face-to-face conversation is held by each two users, a layout in which each four users surround a round table and have interactions, a layout in which four to five users as representatives have interactions inside while the outside is surrounded by a large number of users, and a layout in which about ten users are seated in a circle and perform brainstorming. The facilitator then sets these layouts as patterns of large-frame layouts beforehand in accordance with the number of users, the type of the facilitation method to be implemented, and the like, and layout control can be performed so that the layout from among those patterns is automatically optimized, on the basis of context recognition in the telepresence system 11.

Here, in the telepresence system 11, as a user's recognition through the display device 92 or a device such as virtual reality (VR) goggles, visual information or audio information (layout adjustment for sound source positions, for example) may be presented so that the users at the respective bases 31 surround a round or long table 97, or the users' lines of sight change. With this arrangement, it is possible to provide telepresence in which a mutual space and a user layout that are the best for the users are achieved.

Example Configuration of a Telepresence Apparatus

Figure 9:
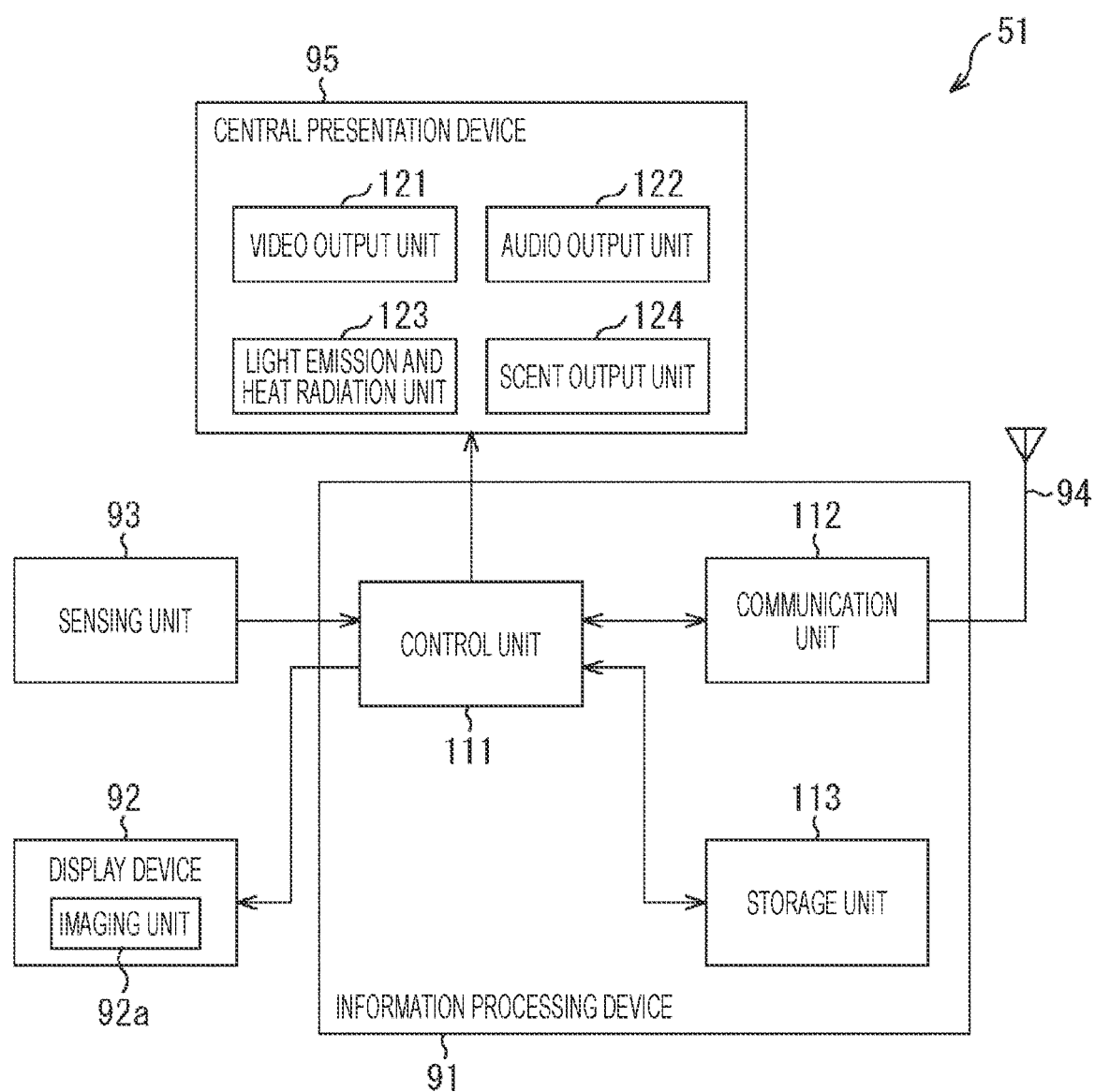
FIG. 9 is a block diagram showing an example configuration of a telepresence apparatus.

Next, FIG. 9 is a block diagram showing an example configuration of a telepresence apparatus 51.

As shown in FIG. 9, the telepresence apparatus 51 includes the information processing device 91, the display device 92, the sensing unit 93, the antenna 94, and the central presentation device 95. Further, the information processing device 91 includes a control unit 111, a communication unit 112, and a storage unit 113.

The control unit 111 includes a processor, a memory, and the like, and controls the entire operation of the telepresence apparatus 51, using various kinds of programs and data stored in the storage unit 113 formed with a hard disc drive (HDD), a solid state drive (SSD), or the like. Also, the control unit 111 performs communication through the network 32 via the communication unit 112, and transmits and receives information to and from the telepresence apparatus 51 at another base 31.

For example, in the telepresence apparatus 51, when the communication unit 112 receives a video image and sound transmitted from the telepresence apparatus 51 at another base 31, the control unit 111 supplies the video image to the display device 92 to display the video image, and outputs the sound from a speaker (not shown).

The control unit 111 then supplies the video image captured by the imaging unit 92a of the display device 92 and the sound collected by a microphone (not shown) to the communication unit 112, and causes the communication unit 112 to transmit the video image and the sound to the telepresence apparatus 51 at the other base 31. The control unit 111 can also share the sensing information supplied from the sensing unit 93 with the telepresence apparatus 51 at the other base 31.

The central presentation device 95 includes a video output unit 121, an audio output unit 122, a light emission and heat radiation unit 123, and a scent output unit 124. The video output unit 121 outputs a stereoscopic video image so that it can be visually recognized from anywhere around central presentation device 95, and the audio output unit 122 outputs the sound matched with the video image being output by the video output unit 121. Likewise, in conjunction with the video image being output by the video output unit 121, the light emission and heat radiation unit 123 outputs light and heat, and the scent output unit 124 outputs a scent.

For example, in the telepresence apparatus 51, a video image of the users A to C at the other base 31 is displayed on the display device 92, and the central presentation device 95 is disposed at the center of the communication space shared with the users D to G at the subject base 31, as described above with reference to FIG. 3. The control unit 111 then controls the output of the video image of the bonfire by the video output unit 121, the output of the sound of the bonfire by the audio output unit 12, the output of the light emission and heat radiation of the bonfire by the light emission and heat radiation unit 123, and the output of the scent of the bonfire by the scent output unit 124.

Further, in the telepresence apparatus 51, the users A to C are sensed by the sensing unit 93 of the other base 31, the users D to G are sensed by the sensing unit 93 of the subject base 31, and these pieces of sensing information are shared. On the basis of the sensing information, the control unit 111 then selects the round-table layout or the alignment layout for the layout of the communication space, and performs control to set the selected layout, as described above with reference to FIG. 8.

Also, as described above with reference to FIG. 8, the control unit 111 performs control so that the round table 97 is used in the round-table layout, and the long table 97-2 is used in the alignment layout. Further, when switching the layouts, the control unit 111 changes the height of the users' lines of sight at each base 31, and performs control so that the users' lines of sight in the round-table layout is lower than the users' lines of sight in the alignment layout.

Telepresence Process

Figure 10:
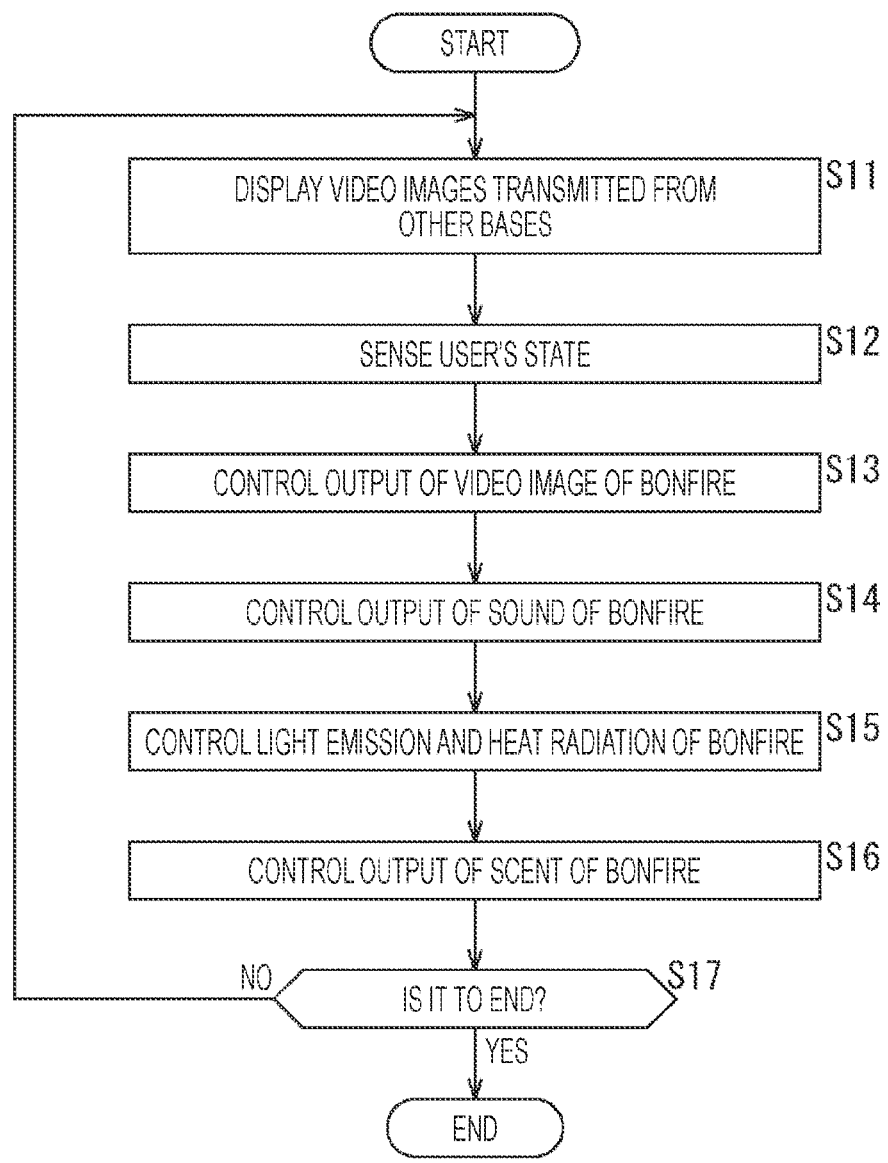
FIG. 10 is a flowchart for explaining a telepresence process.

Referring now to a flowchart in FIG. 10, a telepresence process to be performed in the telepresence apparatus 51 is described. Note that this process is based on the premise that communication between the telepresence apparatuses 51 to mutually perform the telepresence process is established in advance.

In step S11, the control unit 111 receives a video image transmitted from the telepresence apparatus 51 at the other base 31 via the communication unit 112, and causes the display device 92 to display the video image. In parallel with that, the control unit 111 transmits the video image captured by the imaging unit 92a to the telepresence apparatus 51 at the other base 31 via the communication unit 112.

In step S12, the sensing unit 93 senses the users at the subject base 31, and supplies sensing information indicating the result of the sensing to the control unit 111. The control unit 111 then shares the sensing information with the control unit 111 at the other base 31.

In step S13, the control unit 111 controls the output of the video image to the video output unit 121 of the central presentation device 95, and controls the video output unit 121 to output a video image of a bonfire, for example.

In step S14, the control unit 111 controls the output of the sound to the audio output unit 122 of the central presentation device 95, and controls the audio output unit 122 to output a sound of a bonfire, for example.

In step S15, the control unit 111 controls the output of the light emission and heat radiation to the light emission and heat radiation unit 123 of the central presentation device 95, and controls the light emission and heat radiation unit 123 to output light and heat of a bonfire, for example.

In step S16, the control unit 111 controls the output of the scent to the scent output unit 124 of the central presentation device 95, and controls the scent output unit 124 to output a scent of a bonfire, for example.

In step S17, the control unit 111 determines whether or not a process end instruction has been issued. If any end instruction has not been issued, the process returns to step S11. That is, the processes in steps S11 to S17 are repeated until an end instruction is issued.

If it is determined in step S17 that an end instruction has been issued, the process then comes to an end.

As described above, in the telepresence apparatus 51, the central presentation device 95 disposed at the center of a communication space can perform presentation for prompting communication, by outputting a video image, sound, light, heat, and scent of a bonfire, for example. With this arrangement, in the telepresence apparatus 51, users at different bases 31 can share a communication space surrounding a bonfire, for example, and have better communication.

Figure 11:
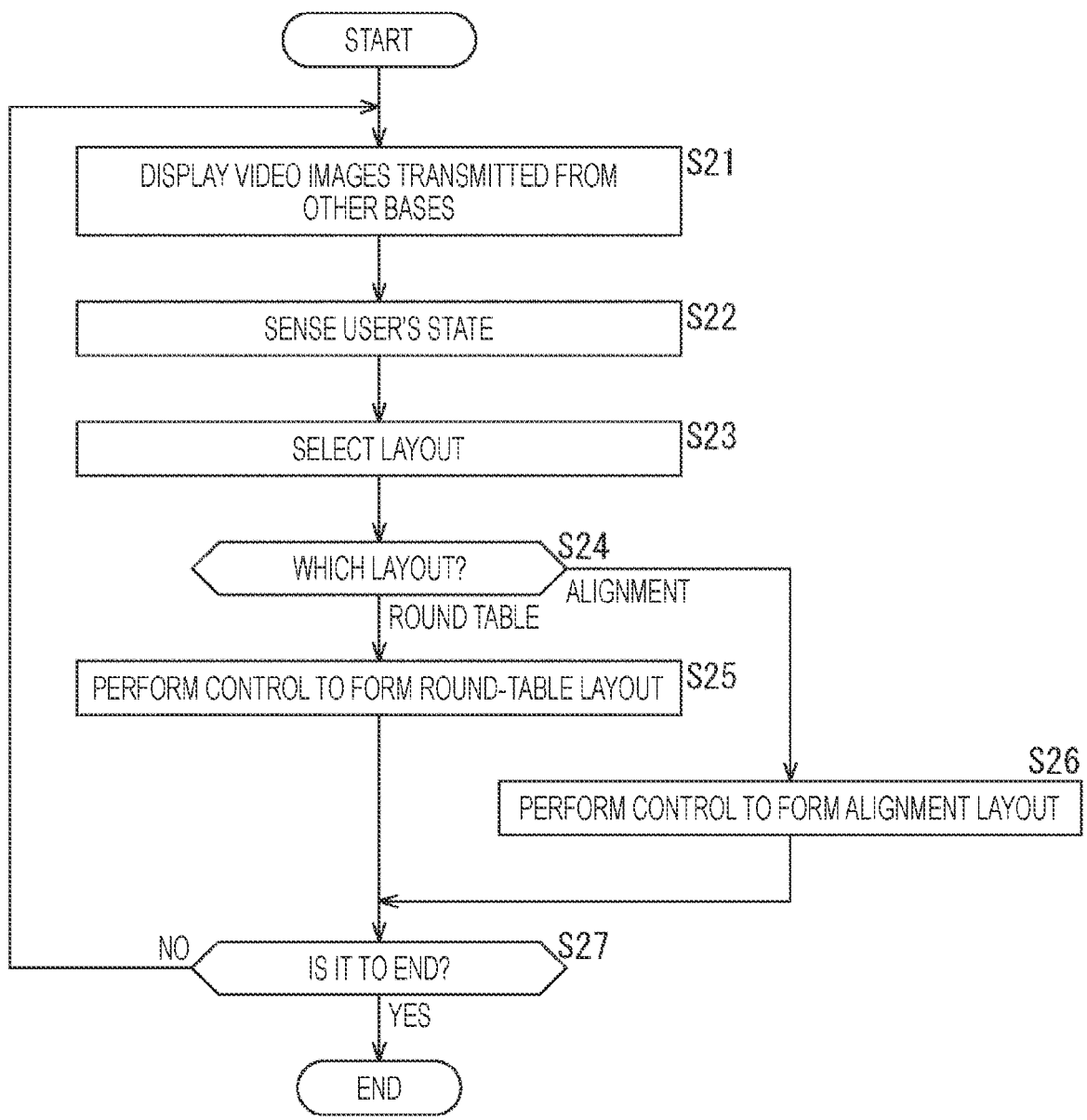
FIG. 11 is a flowchart for explaining a layout switching process.

Referring now to a flowchart in FIG. 11, a layout selection process in a telepresence process to be performed in the telepresence apparatus 51 is described. Note that this process is based on the premise that communication between the telepresence apparatuses 51 to mutually perform the telepresence process is established in advance.

In steps S21 and S22, processes similar to those in steps S11 and S12 in FIG. 10 are performed.

In step S23, the control unit 111 selects the round-table layout or the alignment layout as the layout of the communication space, on the basis of the sensing information supplied from the sensing unit 93 in step S22. For example, on the basis of users' emotions, biological information, various states, and the like, or the context of the communication, various situations, and the like, the control unit 111 selects the round-table layout in a case where it is necessary to perform relaxed communication, and selects the alignment layout in a case where it is necessary to perform intensive communication.

In step S24, the control unit 111 determines whether the layout selected in step S23 is the round-table layout or the alignment layout.

If the control unit 111 determines in step S24 that the round-table layout is selected, the process moves on to step S25, and control is performed to set the round-table layout. Specifically, the control unit 111 performs control so that the round table 97-1 is used, and the users are seated so as to surround the central presentation device 95 at the center, as shown on the upper side in FIG. 8.

If the control unit 111 determines in step S24 that the alignment layout is selected, on the other hand, the process moves on to step S26, and control is performed to set the alignment layout. Specifically, the control unit 111 performs control so that the long table 97-2 is used, and the users are seated along the long table 97-2, as shown on the lower side in FIG. 8.

In step S27, the control unit 111 determines whether or not a process end instruction has been issued. If any end instruction has not been issued, the process returns to step S21. That is, the processes in steps S21 to S27 are repeated until an end instruction is issued.

If it is determined in step S27 that an end instruction has been issued, the process then comes to an end.

As described above, the telepresence apparatus 51 switches between the round-table layout and the alignment layout on the basis of sensing information, and thus, users present at different bases 31 can have better communication.

Examples in which Processes are Carried Out by Software

Meanwhile, the above described series of processes can be performed by hardware, but can also be performed by software. In a case where the series of processes are performed by software, the program that forms the software can be installed in a computer incorporated into special-purpose hardware, or can be installed from a recording medium into a general-purpose computer or the like that can execute various kinds of functions by installing various kinds of programs, for example.

FIG. 12 shows an example configuration of a general-purpose computer. This personal computer includes a central processing unit (CPU) 1001. An input/output interface 1005 is connected to the CPU 1001 via a bus 1004. A read-only memory (ROM) 1002 and a random access memory (RAM) 1003 are connected to the bus 1004.

An input unit 1006, an output unit 1007, a storage unit 1008, and a communication unit 1009 are connected to the input/output interface 1005. The input unit 1006 is formed with an input device such as a keyboard or a mouse through which a user inputs an operation command, the output unit 1007 outputs an image of a process operating screen or a processing result to a display device, the storage unit 1008 is formed with a hard disk drive or the like that stores programs and various kinds of data, and the communication unit 1009 is formed with a local area network (LAN) adapter or the like and performs a communication process via a network that is typically the Internet. A drive 1010 is also connected to the input/output interface 1005. The drive 1010 performs data reading and writing on a removable storage medium 1011, such as a magnetic disk (such as a flexible disk), an optical disk (such as a Compact Disc-Read-Only Memory (CD-ROM) or a Digital Versatile Disc (DVD)), a magnetooptical disk (such as Mini Disc (MD)), or a semiconductor memory.

The CPU 1001 performs various processes in accordance with a program that is stored in the ROM 1002, or a program that is read from the removable storage medium 1011, which is a magnetic disk, an optical disk, a magnetooptical disk, a semiconductor memory, or the like, is installed into the storage unit 1008, and is loaded from the storage unit 1008 into the RAM 1003. The RAM 1003 also stores data and the like necessary for the CPU 1001 to perform various processes, as appropriate.

In the computer having the above described configuration, for example, the CPU 1001 loads a program stored in the storage unit 1008 into the RAM 1003 via the input/output interface 1005 and the bus 1004, and executes the program, so that the above described series of processes are performed.

The program to be executed by the computer (the CPU 1001) can be recorded on the removable storage medium 1011 as a packaged medium or the like, for example, and be then provided. Alternatively, the program can be provided via a wired or wireless transmission medium, such as a local area network, the Internet, or digital satellite broadcasting.

In the computer, the program can be installed into the storage unit 1008 via the input/output interface 1005 when the removable storage medium 1011 is mounted on the drive 1010. Also, the program can be received by the communication unit 1009 via a wired or wireless transmission medium, and be installed into the storage unit 1008. Alternatively, the program can be installed beforehand into the ROM 1002 or the storage unit 1008.

Note that the program to be executed by the computer may be a program for performing processes in chronological order in accordance with the sequence described in this specification, or may be a program for performing processes in parallel or performing a process when necessary, such as when there is a call.

Note that the CPU 1001 in FIG. 12 achieves the functions of the control unit 111 shown in FIG. 9.

Also, in this specification, a system means an assembly of plurality of components (devices, modules (parts), and the like), and not all the components need to be provided in the same housing. In view of this, a plurality of devices that are housed in different housings and are connected to one another via a network forms a system, and one device having a plurality of modules housed in one housing is also a system.

Note that embodiments of the present disclosure are not limited to the above described embodiments, and various modifications can be made to the embodiments without departing from the scope of the present disclosure.

For example, the present disclosure can be embodied in a cloud computing configuration in which one function is shared among devices via a network, and processing is performed by the plurality of devices cooperating with one another.

Further, the respective steps described with reference to the flowcharts described above can be carried out by one device, or can be shared among a plurality of devices.

Furthermore, in a case where a plurality of processes is included in one step, the plurality of processes included in the one step can be performed by one device, or can be shared among a plurality of devices.

Note that, as long as there is no inconsistency, the plurality of technologies described in this specification can be implemented independently of one another. It is of course also possible to implement a combination of some of the plurality of techniques according to the present technology. For example, part or all of the present technology described in one of the embodiments can be implemented in combination with part or all of the present technology described in another one of the embodiments. Further, part or all of the present technology described above can be implemented in combination with some other technology not described above.

Example Combinations of Configurations

Note that the present technology can also be embodied in the configurations described below.

(1)
A telepresence system including:
a network that connects a plurality of bases; and
a plurality of telepresence apparatuses that transmit and receive a video image and sound via the network, and share the video image and the sound between the respective bases, in which,
in each of the telepresence apparatuses, a presentation device that performs presentation for prompting communication by users at different bases is disposed at a center of a shared communication space in which the users communicate with each other.

(2)
The telepresence system according to (1), in which
the presentation device is disposed at a center of gravity of a figure that is formed with external straight lines connecting a plurality of the users sharing the communication space.

(3)
The telepresence system according to (1) or (2), in which
the users sharing the communication space are placed at substantially equal intervals, with the presentation device at the center.

(4)
The telepresence system according to any one of (1) to (3), in which
the presentation device includes a video output unit that outputs a stereoscopic video image visually recognizable from anywhere around the presentation device.

(5)
The telepresence system according to (4), in which
the presentation device further includes an audio output unit that outputs sound matched with the video image being output by the video output unit.

(6)
The telepresence system according to (4) or (5), in which
the presentation device further includes a light emission and heat radiation unit that outputs light and heat matched with the video image being output by the video output unit.

(7)
The telepresence system according to any one of (4) to (6), in which
the presentation device further includes a scent output unit that outputs a scent matched with the video image being output by the video output unit.

(8)
The telepresence system according to any one of (1) to (7), in which
the presentation device presents a video image, sound, light, heat, and a scent of a bonfire to a user performing communication using the telepresence apparatus.

(9)
The telepresence system according to any one of (1) to (8), in which
the presentation device displays information to be shared by all users in the communication space.

(10)
The telepresence system according to any one of (1) to (9), in which
a ratio between regions occupied by the plurality of bases is changeable in the communication space.

(11)
The telepresence system according to any one of (1) to (10), in which,
when video images of the plurality of bases are displayed on a display device, a ratio between regions displaying the respective video images is dynamically changeable.

It should be noted that this embodiment is not limited to the above described embodiments, and various modifications may be made to them without departing from the scope of the present disclosure. Furthermore, the advantageous effects described in this specification are merely examples, and the advantageous effects of the technology are not limited to them and may include other effects.

REFERENCE SIGNS LIST

11 Telepresence system
31 Base
32 Network
51 Telepresence apparatus
71 Office building
91 Information processing device
92 Display device
93 Sensing unit
94 Antenna
95 Central presentation device
96 Personal computer
96, 97 Table
111 Control unit
112 Communication unit
113 Storage unit
121 Video output unit
122 Audio output unit
123 Light emission and heat radiation unit
124 Scent output unit

The invention claimed is:

1. A telepresence system, comprising:
a network configured to connect a plurality of bases; and
a plurality of telepresence apparatuses configured to:
   transmit a video image and sound via the network; and
   receive the video image and sound via the network,
wherein,
   in each of the plurality of telepresence apparatuses, a presentation device that is configured perform presentation for prompting communication by a plurality of users at different bases is at a center of a shared communication space in which the plurality of users communicate with each other,
   the presentation device includes a video output unit configured to output a stereoscopic video image visually recognizable from anywhere around the presentation device, and
   the presentation device further includes a light emission and heat radiation unit configured to output light and heat matched with the stereoscopic video image output by the video output unit.

2. The telepresence system according to claim 1, wherein the presentation device is at a center of gravity of a figure that is formed with external straight lines connecting the plurality of users sharing the shared communication space.

3. The telepresence system according to claim 2, wherein the plurality of users sharing the shared communication space are placed at equal intervals, with the presentation device at the center.

4. The telepresence system according to claim 1, wherein the presentation device further includes an audio output unit configured to output the sound matched with the video image output by the video output unit.

5. The telepresence system according to claim 1, wherein the presentation device further includes a scent output unit configured to output a scent matched with the video image output by the video output unit.

6. The telepresence system according to claim 1, wherein the presentation device is further configured to present the video image, the sound, the light, the heat, and a scent of a bonfire to a user performing communication using a telepresence apparatus of the plurality of telepresence apparatuses.

7. The telepresence system according to claim 1, wherein the presentation device is further configured to display information shared by the plurality of users in the shared communication space.

8. The telepresence system according to claim 1, wherein a ratio between regions occupied by the plurality of bases is changeable in the shared communication space.

9. The telepresence system according to claim 1, wherein, when video images of the plurality of bases are displayed on a display device of a telepresence apparatus of the plurality of telepresence apparatuses, a ratio between regions displaying respective video images is dynamically changeable.

* * * * *